United States Patent [19]
Reitz et al.

[11] Patent Number: 5,517,114
[45] Date of Patent: May 14, 1996

[54] APPARATUS FOR TESTING ELONGATED OBJECTS HAVING A RADIALLY ADJUSTABLE ROTARY PROBE

[75] Inventors: Helmut Reitz, Metzingen; Helmut Schwarz, Kusterdingen; Heinrich Braun, Reutlingen, all of Germany

[73] Assignee: Institut Dr. Friedrich Forster Prufgeratebau GmbH & Co. KG, Reutlingen, Germany

[21] Appl. No.: 245,894

[22] Filed: May 19, 1994

[30] Foreign Application Priority Data

Jul. 20, 1993 [DE] Germany .......................... 43 24 332.0

[51] Int. Cl.⁶ .................................................. G01N 27/90
[52] U.S. Cl. ...................... 324/262; 324/232; 324/242
[58] Field of Search ..................................... 324/226, 232, 324/237, 238, 240–243, 262; 73/622, 637, 638

[56] References Cited

U.S. PATENT DOCUMENTS 3,612,987  10/1971  Placke et al. .
4,053,827  10/1977  Millette et al. .

FOREIGN PATENT DOCUMENTS 3314377   11/1983  Germany .
3739190   6/1989   Germany .
9108162   12/1991  Germany .
4121948   1/1993   Germany .
968728    10/1982  U.S.S.R. .
1089505   4/1984   U.S.S.R. .
1280515   12/1986  U.S.S.R. .

OTHER PUBLICATIONS

*Rotary–Probe Eddy Current Testing of Hot Steel Rods*, M. Mizuno, "Material Evaluation", Jun. 1991, pp. 681–684.

*Primary Examiner*—Gerard R. Strecker
*Attorney, Agent, or Firm*—Bell, Seltzer, Park & Gibson

[57] ABSTRACT

A device for testing elongated objects, particularly wires, optionally with cross-sectional irregularities, which has a rotating test head traversed by the object and on which is provided a probe, particularly an eddy current probe, provided on rotary probe holding means and guided on circular paths about the object. For the change of the radial spacing between the object and the probe with the test head rotating, externally controllable e.g. by a sensor for irregularities, the device has a switching device with two inherently stable switching states, whereof one can correspond to a testing position near the object and another to a raised position further removed from the object and which can be rapidly set for protecting the probes.

16 Claims, 6 Drawing Sheets

APPARATUS FOR TESTING ELONGATED OBJECTS HAVING A RADIALLY ADJUSTABLE ROTARY PROBE

BACKGROUND OF THE INVENTION

The invention relates to a device for testing elongated objects, particularly wires, which may possibly have cross-sectional irregularities, with a rotary test head through which passes an object having at least one probe, more particularly in the form of an eddy current probe, on partly movable probe holding means and guided on circular probe paths around the object and, in the case of a rotating test head, externally operable switching or indexing device for modifying the radial spacing between the object and the probe. The invention more particularly relates to the problem of protecting sensitive probes with high rotation speeds guided close to the surface of an object passing through the test head when cross-sectional irregularities occur against contact with the object and therefore against destruction, in that they are moved back in good time and rapidly from a testing position near the object into a raised position further away from the object. Particularly in the case of cross-sectional irregularities with a limited axial extension, such as occur e.g. in the form of weld beads or sharp-edged shoulders in the case of welded wires in continuously operated wire drawing plants, the probes, after the test head has passed through the critical areas of the object, are to be returned with high reproduction accuracy into the testing position near the object.

DESCRIPTION OF THE PRIOR ART

Tests or inspections for surface errors are an important part of the quality control when producing metallic semi-finished products, such as pipes, bars or wires. The aim is in particular an uninterrupted inspection of the surfaces with high resolution, even for small faults, e.g. cracks with a depth of a few tenths of a mm, in cyclic manner and with the speed of the manufacturing process. Nowadays such tests are frequently performed using rotary probe eddy current technology, in which an eddy current probe is guided at a high rotation speed at a distance of 1 to 2 mm from the surface of an object passing through a rotary test head of a test device and the surface is inspected along a spiral scanning path passing spirally around the traversing object.

There is a risk of the probes being destroyed, where on the test object there are irregularities with respect to the centricity and/or cross-section of the same order of magnitude of the testing spacing, because a contact between the probe and the object could lead to damage to the test device.

A known rotary probe test device, in which the probes can be removed from their testing position at test head rotation speeds of up to 1800 r.p.m. is described in "Material Evaluation", 6, 1991, pp 681 to 684. On a test machine for connection to rolling devices for steel bars a raising or lifting device raises the test heads, before passage through the test head of irregularly deformed or shaped ends of rolled steel bars no longer passing centrally through the testing device. The raising device has two disks of different diameters rotating concentrically around the object rotatable with respect to one another about a common central axis. Two lever-like probe holding means in each case carrying a probe are mounted in rotary manner in rotationally symmetrical manner facing one another close to the outer circumference of the inner disk. Lever pins fitted to the outer disk engage in elongated holes in the levers remote from the lever rotation axis. The position of the levers, in which the lever pins, rotation axis and probe are located on a line running tangentially to the object and therefore also to the position of the probes with respect to the object, remains unchanged for as long as both disks rotate at the same speed.

If there is an irregularity in the object cross-section, which is detected by means of a sensor, the latter activates a hydraulic brake, which mechanically engages on the outer disk and slows down its rotary movement. This leads to a relative movement of the outer disk with respect to the inner disk counter to the rotation direction of the test head in such a way that the lever pins fitted to the outer disk and engaging in the elongated holes of the lever rotate the probe levers about their rotation axis. During this rotation the probes fitted to the other side of the lever are raised. The relative reciprocal rotation of the two disks is limited by stop pins fitted to the levers. On releasing the brake the relative rotation of the two disks with respect to one another is cancelled out and the test heads return to their testing position.

Such raising or lifting devices with frictional contact between mechanical brakes and rotating disks cannot be used, or can only be used when accepting high material wear and the resulting maintenance costs, for much higher rotational speeds of test heads, such as occur in modern testing machines for high throughputs, which can e.g. be up to 9000 r.p.m. or higher. If long raising times are required, which can e.g. be the case with axially elongated or extensive faults, due to production machine errors, the raising action requires longer action times on the part of the brakes, which in certain circumstances can lead to a deceleration of the complete test head and therefore increased wear to functionally important parts.

SUMMARY OF THE INVENTION

The problem of the invention is to provide a raising device for test heads operating with limited maintenance and wear and suitable for test heads which may rotate at very high rotational speeds and which obviates the aforementioned disadvantages. In particular, in the case of this raising device the time between the detection of relevant cross-sectional changes to the object and the raising or return of the probes must be constant and relatively short, the return or resetting to the test position must take place with high reproduction precision and randomly long raising actions must be possible without energy expenditure.

The invention leads to a switching or indexing device, which permits a switching over between two energy-equivalent, stable switching or indexing states. In the present context stable means that the switching states can be maintained without additional energy expenditure from the outside, particularly with the test head rotating and for randomly long times. In one stable switching state corresponding to the testing position of the switching device, the probes rotating about an object passing through the test head are at a precisely determinable, limited spacing of typically 1 to 2 mm from the object surface. In another stable switching state the distance between the surface of the traversing object and the probes is much larger, e.g. 4 to 5 mm. The probes can be rapidly moved away from the object into this raised position by means of the switching device. Each switching state corresponds to a geometrically precisely defined reciprocal configuration of the individual parts of the switching device.

Switching devices in rapidly rotating test heads are subject to radially outwardly directed centrifugal forces during rotation and which can easily be several thousand times the acceleration due to gravity. In the case of the switching device according to the invention it is particularly advantageous that the individual control elements of the switching device are so positioned that the arrangement of the partially interengaging control elements cannot be moved by the centrifugal forces alone.

Therefore the arrangement of the control elements is neutral with respect to centrifugal forces. This excludes any unintentional adjustment of the switching device due to the centrifugal forces, even in the case of very high test head rotation speeds.

The switching over or reversing of the switching device can take place by a mechanical switching or reversing means acting on the arrangement of the control elements and which in interaction with the latter has two inherently stable switching states. For the operation of the switching over or reversing means in the case of a rotating test head, it is particularly advantageous that the reversing means can be stabilized by the centrifugal forces occurring when the test head is rotated.

As a result of the arrangement of the control elements being neutral with respect to centrifugal forces and the reversing means being stabilizable by centrifugal forces and acting thereon, a switching device is created, which does not simply develop further solutions for switching devices for stationary or slowly rotating systems, so as to make them relatively insensitive to the centrifugal forces occurring in rapidly rotating systems. Instead, the special conditions of rapidly rotating systems are utilized for a novel switching device optimally adapted to fast rotating devices.

In a preferred embodiment of the invention it is particularly appropriate to rotatably mount the individual control elements of the switching device, which partly act on one another close to and in particular on the centre of gravity or mass centre thereof. Thus, for each control element the sum of the torques brought about by the centrifugal forces and acting directly thereon disappears. Control elements mounted in this way have no preferred position, i.e. for maintaining a specific rotary position, even when the test head is rotating, no force need be expended. The same also applies for an arrangement of control elements partly acting on one another, if each of the control elements is mounted neutrally with respect to centrifugal forces.

If a reversing means acts on one of these control elements and rotates the same, apart from the force to be applied for the rotational acceleration of the individual control elements the only disturbing forces to be overcome are the frictional forces occurring in the mounting supports and in the action or engagement points of the control elements. Particularly in the case of lightweight control elements, the energy to be applied for the reversing of the arrangement of control elements is relatively small.

Another major advantage of such a bistable switching device, in which both switching states are stable without any energy supply, is that only during the reversing or switching over process does there have to be an action from the outside on the switching device. In a preferred embodiment only a short energy pulse is required for reversing or switching over. This energy pulse can be transferred by a contactless-operating energy pulse transmitting means, particularly by one or more eddy current brakes, in the form of braking energy to a rotating member, preferably a disk, brakeable by eddy current brakes.

This type of contactless influencing of the switching device from the outside is adapted in a particularly advantageous manner to the operating conditions in rapidly rotating test heads. Due to the fact that between a moving part to be decelerated, e.g. a rotating disk, and a stationary eddy current brake no contact exists, a braking process can be performed randomly frequently in wear-free manner. This obviates maintenance to the testing device, namely for replacing brake linings or disks. This is particularly advantageous in the case of testing devices intended for continuous use, e.g. in continuously operating wire drawing plants, in which following the "running in" of the plants any stoppage can lead to considerable production losses.

It is also advantageous that in the case of eddy current brakes with increasing rotational speed of the parts to be decelerated by them their action is increased. As mentioned hereinbefore, the reversing process of the switching device only requires limited energy expenditure, but the latter increases with the increasing rotational speed of the test head. However, this is compensated by the action of an eddy current brake which also rises with the rotational speed.

The immediate objective of the switching process, i.e. the modification of the spacing between the probe and the object, particularly during operation, can appropriately be brought about by rotating at least one probe holding means, to which a probe can be fitted. The probe holding means can be in the form of a mass-compensated lever, the centre of gravity of the lever holding the probe preferably precisely coinciding with the rotation or bearing axis of the lever. In the case of a lever mounted in this way, even in the case of high test head speeds, on whose rotor the lever is mounted, there are no unintentional adjustments as a result of centrifugal forces and such levers can be easily rotated even in the case of high head speeds. This more particularly applies with lightweight constructions of the levers, which are e.g. made from twist-resistant, lightweight components, such as flat carbon fibre materials.

For using the testing machine for test objects having different diameters, it is particularly appropriate that the probe holding means with the probes are designed in such a way that the probes over a limited rotation area of the probe holding means are arranged with their optimum action zone radially to the passage axis of the object. Thus, in the case of an identical spacing between the probe and the object surface, the measuring conditions for objects with different diameters are substantially the same with respect to the probe action. If the optimum action range of the probes, such as in the elongated probes of the preferred embodiment, is on the longitudinal axis of the probe, then a vertical position of the probe with respect to the object surface, in which the longitudinal axis of the probe is arranged radially with respect to the object, can be achieved in that the probe longitudinal axis is perpendicular to a tangent plane on the object circumference of an object having an average diameter passing through the rotation axis of the probe holding means. In the case of objects whose diameter does not differ so greatly from the average diameter, the probe longitudinal axis is always positioned approximately radially to the test object, but in such a way that the action range of the probe is still oriented in an optimum manner with respect to the object.

The approximately radial orientation of the probe with different test object diameters is of minor importance during the raising of the probes, because no measurement has to take place in the raised state. However, it is advantageous if for the testing device the diameter of the probe circular path desired for testing purposes is adjustable. In a preferred embodiment of the testing device this diameter adjustment of the probe path can be brought about by rotating an adjustment means, which is arranged coaxially with the test head and rotatable with respect thereto. The adjusting means, preferably constructed in the form of a disk, can have spiral segment grooves passing in spiral segmental manner about the adjusting means rotation axis, in which the radial spacing between the groove and the rotation axis of the adjusting means changes along the longitudinal direction of the groove. Coupling means, preferably constructed as pins, can engage in these spiral segment grooves. The pins are located on the probe holding levers remote from their rotation or bearing axes, the mounting supports of the probe holding lever being fixed with respect to the test head on the rotor of the latter. On rotating the adjusting means with respect to the test head rotor about the common rotation axis, the coupling pins run in lateral clearance-free manner along the longitudinal direction of the spiral segment grooves, the coupling pins, as a function of the rotation direction of the adjusting means being moved radially on the rotation axis of the test head either towards or away from the latter. If a coupling pin engages on the side of a probe holding lever to which a probe is also fitted, then a movement of the coupling pin towards the test head rotation axis also brings about a movement of the probe towards the rotation axis. If the rotation direction of the adjusting means with respect to the test head rotor is reversed, then the probe moves roughly radially outwards away from the test head rotation axis.

The diameter adjustment of the probe circular path by means of a preferably disk-like adjusting means can therefore take place solely by rotating interengaging control elements being neutral with respect to centrifugal forces. The total amount of the possible rotation of the adjusting means with respect to the test head can be limited by the length of the spiral segment groove. It is advantageous in the case of spiral segment grooves, particularly those having small pitches, that a desired diameter of the probe circular path can be set at a very high accuracy level, because a small rotation error of the adjusting means only has a minimum effect for the radial position of the probe.

This principle of adjusting the diameter of the probe circular path by rotating an adjusting means is used in the case of the testing device for the switching device for raising the probes from the object.

The setting of the adjusting means in the testing position, i.e. the adaptation of the testing device for the testing or inspection of an object having a given diameter, can be brought about, using internally and/or externally operable setting means, by rotating a preferably disk-like adjusting drive, which in the case of a stationary test head motor can be positively coupled to the adjusting means, can be rotated jointly with the latter with respect to the test head rotor and which in the case of a rotating test head rotor cannot be rotated with respect to the rotor. In the case of rotation of the test head rotor the adjusting means and adjusting drive can be decoupled by a centrifugal force decoupling, so that the adjusting means is rotatable with respect to the rotor and the adjusting drive.

The amount of the relative rotation of the adjusting means with respect to the adjusting drive can be limited by a circular segment groove provided in the latter and in which engages a coupling pin or the like located on the adjusting means, so that the latter is only rotatable with respect to the adjusting drive by a specific control angle. This limited rotation of the adjusting means relative to the adjusting drive and therefore relative to the test head rotor, brings about a clearly defined change of the radial position of the probes. The relative rotation of the adjusting means with respect to the adjusting drive in one direction can be achieved by a brief deceleration or braking, a relative rotation in the opposite direction by a brief acceleration of the adjusting means relative to the rotating adjusting drive.

A braking of the adjusting means, i.e. a brief slowing down of the rotary movement in the rotation direction, can particularly advantageously be brought about e.g. by the action of an eddy current brake on the adjusting means. An acceleration, i.e. a brief increase of the rotary speed in the rotation direction, which can bring about a movement of the adjusting means back to a rotation position present as prior to braking, can be achieved by braking a control means which is also brakeable by an eddy current brake and which can be constructed in the form of a disk arranged coaxially to the adjusting means and rotatable with respect to the latter. If the in particular disk-shaped adjusting means and the disk-shaped control means are coupled in such a way that a rotation of the disk brings about a relative rotation of the other disk in the opposite direction, then by braking the control disk an acceleration of the adjusting means can be brought about.

Such a rotation direction reversal coupling can e.g. be achieved by means of reversing disk or wheels located between the adjusting means and the control means and acting thereon in positive and/or non-positive manner. However, it is particularly advantageous to have a reversing member, particularly a reversing lever, acting on both control elements and mounted in rotary manner on the adjusting drive and which is a component of the centrifugal force stabilized reversing means and during the rotation thereof about its bearing axis the adjusting means and the control means rotate in opposition relative to one another. By a rotation direction reversal coupling a deceleration of a disk can bring about a relative acceleration of the other disk coupled thereto.

For modifying the rotational speed of a rotating component, particularly a disk, other means are also possible. It is particularly advantageous that in the case of a switching device according to the invention for the switching process only a very short action time on the switching device is required.

Thus, rotational speed modifying means are conceivable, which are briefly and therefore in low-wear manner brought into contact with the disk to be influenced and in the case of the rotational speed modifying means in the contact area and at the contact time the path speed component in the rotation direction of the disk to be influenced is smaller than that of the disk in the contact area.

It is also possible to accelerate the rotary movement of a rotating disk, if the corresponding speed component of a rotation speed modifying means at the contact time in the contact area is larger than that of the disk. It would therefore be possible to use for the deceleration or acceleration of the disk e.g. a control disk, whose circumferential speed differs from that of the disk to be influenced and whose circumference engages on the circumference of said disk. In the case of a brief contact between the two disks, the amounts of the circumferential speeds would attempt to approach one another. If the circumferential speed of the control disk in the rotation direction is lower than that of the disk to be decelerated, then said disk undergoes deceleration. Conversely there is an acceleration of the disk to be influenced, if the circumferential speed of the control disk in the rotation direction is higher than that of the disk to be influenced.

A deceleration or acceleration of a suitably designed rotating disk can also be achieved pneumatically, in that the circumferential area of the disk is designed like a water wheel and onto which compressed gas is blown approximately tangentially at at least one point. In the case of a blowing in direction counter to the rotation direction of the disk, the latter can be decelerated, whereas when the blowing is in direction with the rotation direction it can be accelerated.

A deceleration or acceleration of a rotating disk can also be achieved without any action from the outside by using the angular momentum of a rotary disk, in that the inertia moment of the disk is modified by changing the mass distribution in said disk. As in the case of a pirouette of a figure skater a slowing down of a rotary movement can be achieved by the displacement of the mass radially outwards or an acceleration of the rotary movement can be achieved by displacing the mass radially inwards, the disk mass remaining unchanged. Thus, effectively radially outwardly or inwardly displaceable mass pieces, which are e.g. guided within the disk in guide rails and could be moved by electromagnets acting thereon could therefore be used for decelerating or accelerating the rotary movement of a disk.

These and other features can be gathered from the claims, description and drawings, in which the individual features, either singly or in the form of subcombinations, can be realized in an embodiment of the invention and in other fields and can represent advantageous, independently protectable constructions for which protection is hereby claimed. An embodiment of the invention is described in greater detail hereinafter relative to the drawings:

DESCRIPTION OF THE PREFERRED EMBODIMENT

Figure 1:
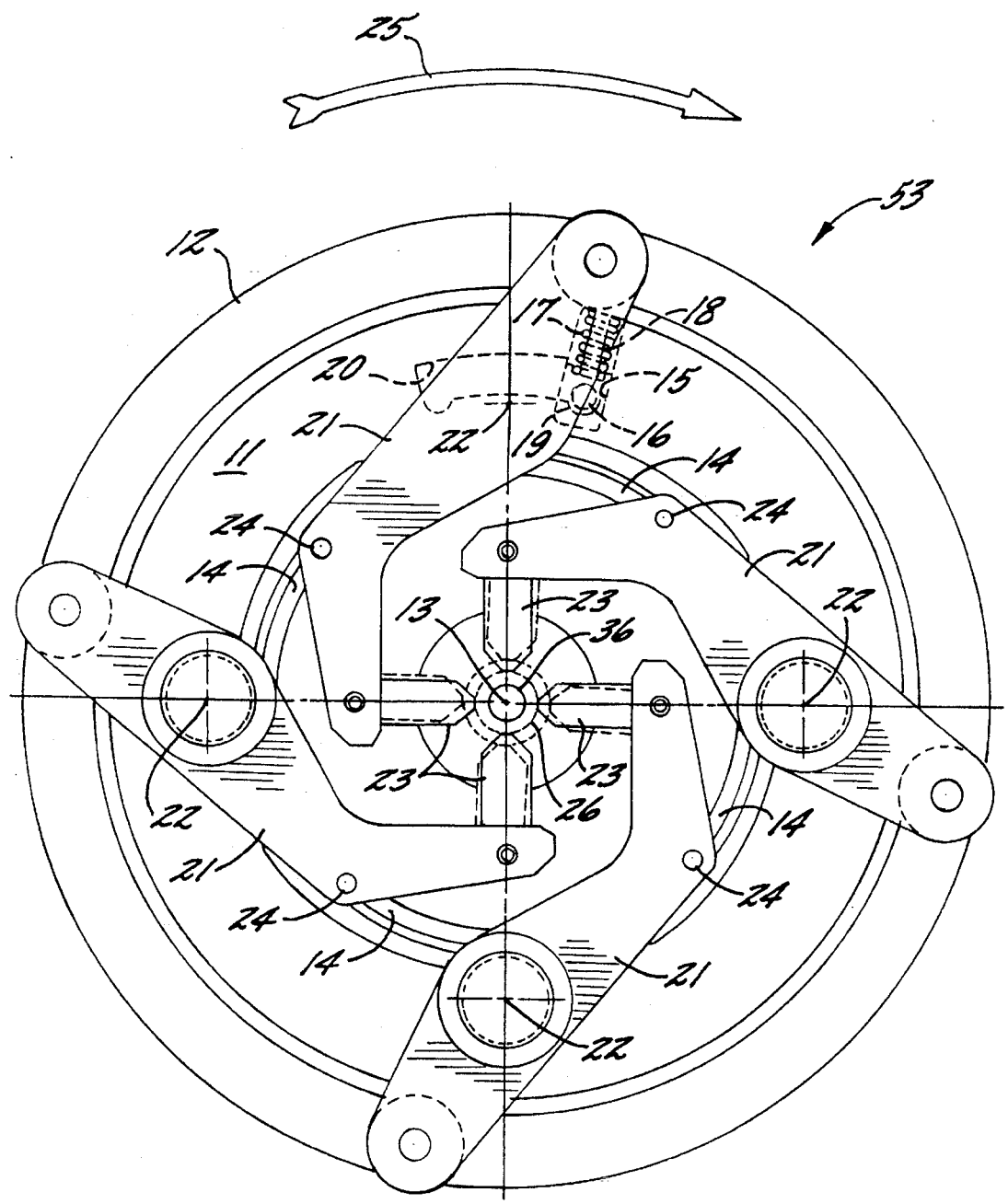
FIG. 1 A front view of functionally important parts of the switching device.

Referring more particularly to the drawings, FIG. 1 illustrates the functionally significant parts of a rotary test head which includes a switching device 53 and which embodies the present invention. The switching device 53 includes an adjusting means in the form of a spiral or control disk 11 and an adjusting drive in the form of a diameter setting disk 12 which are arranged in a rotary manner so as to be coaxial about the axis 13 of the test head. A test object 36 is adapted to run parallel to the test head axis through said head. The spiral disk 11 has four, partly juxtaposed spiral segment grooves 14 of finite length, which are in each case arranged in rotationally symmetrical manner to the test head axis 13 reciprocally displaced by 90°. In the outer area of the spiral disk 11 is provided an elongated hole-like recess 15, whose longitudinal axis passes in the radial direction of the spiral disk 11. In said recess 15 is located a centrifugal force coupling pin 16 displaceable radially therein and whose radial outward movement acts firstly against a coupling spring 17 and then a stop pin 18 located within said spring. In the case of a stationary or slowly rotating test head rotor, the centrifugal force coupling pin 16 is forced by the coupling spring 17 into a recess 19 directed towards the head axis 13 in a circular segment groove 20 in the diameter setting disk 12. Therefore the spiral disk 11 and the diameter setting disk 12, when the test head is stationary, are positively coupled and simultaneously rotatable with one another.

On the test head rotor in rotationally symmetrical manner are rotatably mounted four probe holding means constructed as mass-compensated probe holding levers 21 and which are reciprocally displaced by 90°, which are mounted so as to rotate on the rotor about their lever rotation axis 22 and in an end region thereof is fitted a probe 23, whose longitudinal axis is substantially radial to the test head axis. On the probe side of each probe holding lever 21 is located a coupling pin 24 and in each case one coupling pin 24 engages in a spiral segment groove 14 of the spiral disk 11. In the represented reciprocal position of the control elements 11, 12, 21 and a rotation of the test head in the direction given by the rotation direction arrow 25, the active areas of the probes rotate on a circular test path 26 about the test object.

Figure 2:
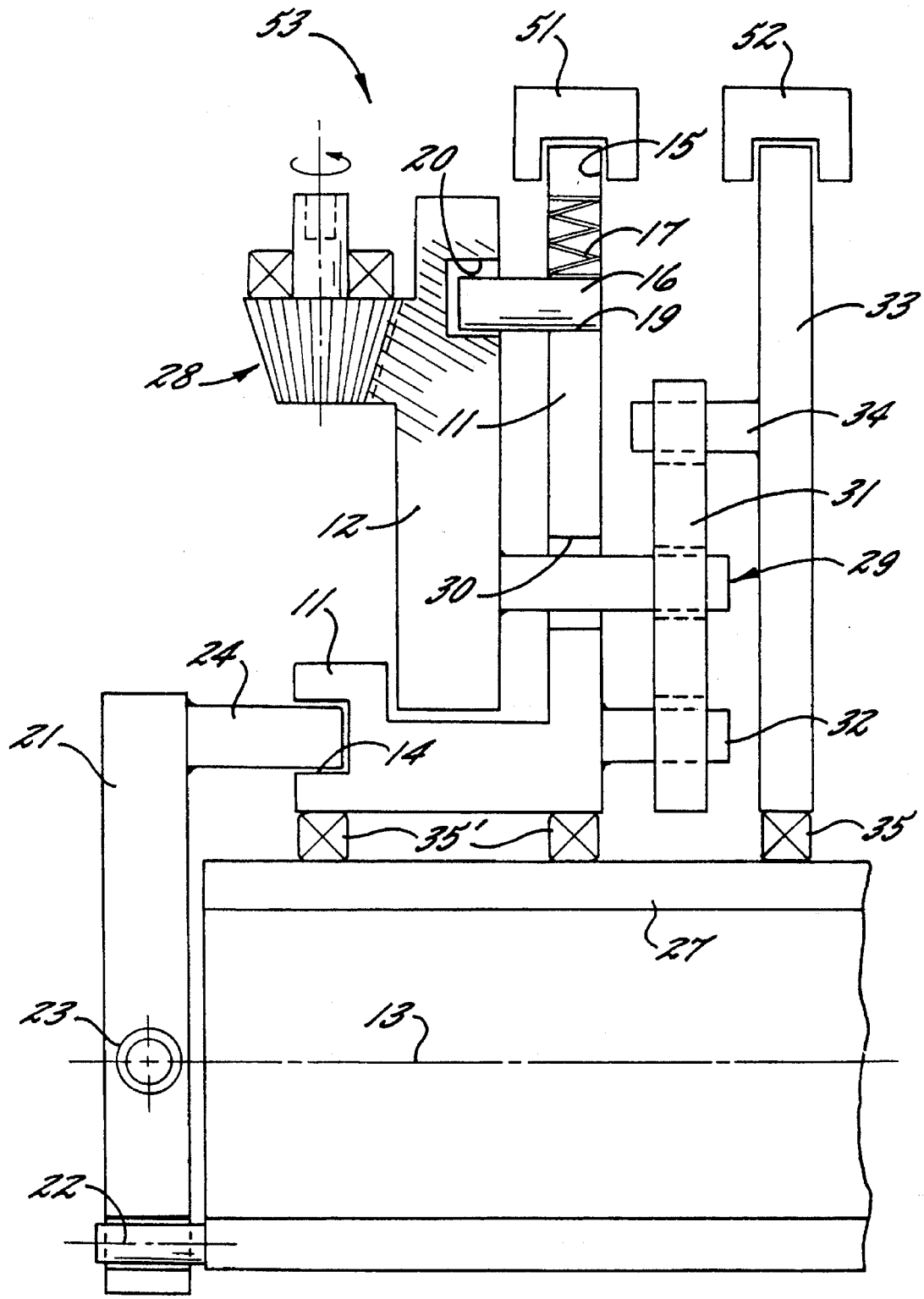
FIG. 2 A diagrammatic side view of the switching device.

The diagrammatic side view of FIG. 2 illustrates how the control elements of the switching device are successively arranged in the direction of the test head axis 13, which also corresponds to the rotation axis of the rotor 27. It can be clearly seen how a coupling pin 24 of a probe holding lever engages in a spiral segment groove 14 of the spiral disk 11, the latter being rotatably mounted with respect to the rotor 27 by spiral disk bearings 35'. Adjacent to the coupling spring 17 in the recess 15 of the spiral disk 11 is provided the centrifugal force coupling pin 16, which engages in a circular segment groove 20 of the diameter setting disk 12.

The adjustment of the diameter setting disk 12 and the spiral disk 11 positively coupled thereto via the centrifugal force coupling pin 16 relative to the rotor 27 is adjustable by means of an adjusting means constructed as a frustum rack and pinion drive 28, which engages in a corresponding tooth system of the diameter setting disk 12. This adjustment of the diameter setting disk can take place manually with the test head stationary, but also automatically and internally by means of correspondingly controllable motors. A reversing means journal 29 is firmly connected to the diameter setting disk and passes through a recess 30 in the spiral disk 11 and is mounted in rotary manner on a reversing or change lever 31. The change lever 31 engages by means of a spiral disk journal 32 fixed to the spiral disk 11 and by means of a switching disk journal 34 fixed to the switching disk 33 on the latter, which by means of switching disk bearings 35 is rotatably mounted coaxially with respect to the rotor 27.

Close to the outer circumference of the spiral disk 11 is provided a spiral disk eddy current brake 51 and close to the outer circumference of the switching disk 33 a switching disk eddy current brake 52 in such a way that in the case of a brief "actuation" of an eddy current brake, i.e. by a current pulse, the in each case influenced disk 11 or 13 can undergo a brief deceleration of its rotary movement.

Figure 3:
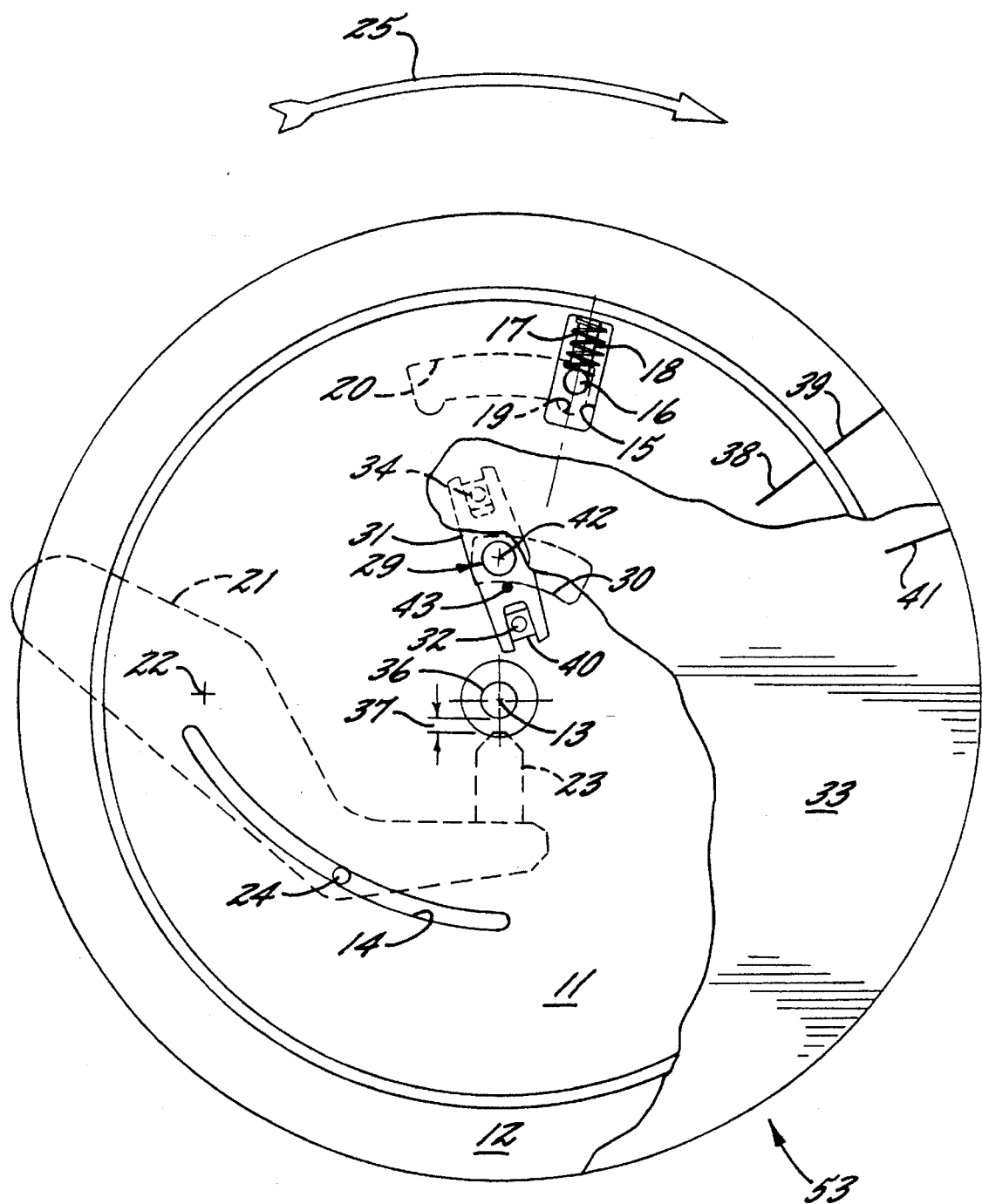
FIG. 3 A diagrammatic representation of the switching device in the testing position.
Figure 4:
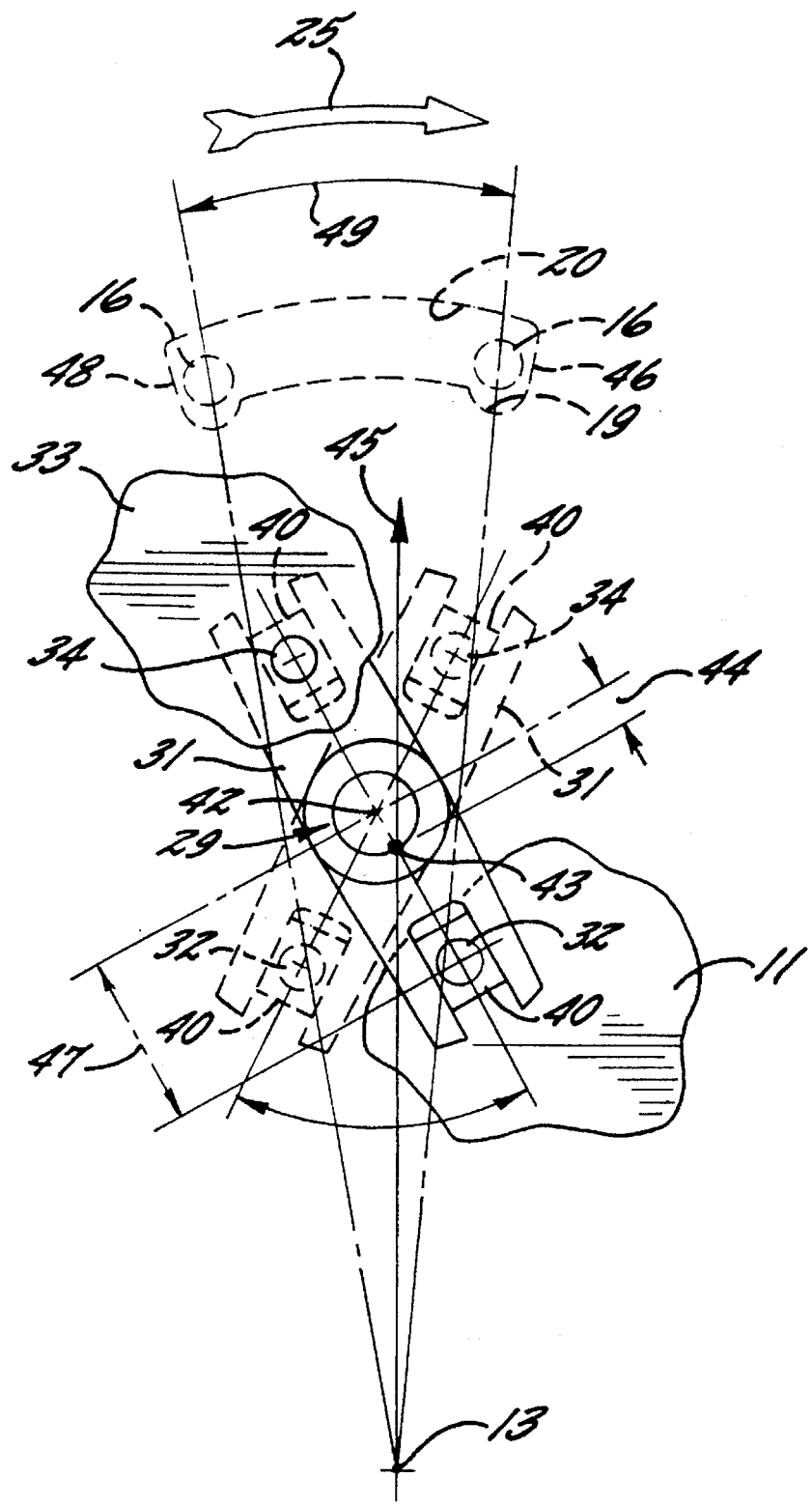
FIG. 4 A diagrammatic representation of the operation of the bistable reversing means.
Figure 5:
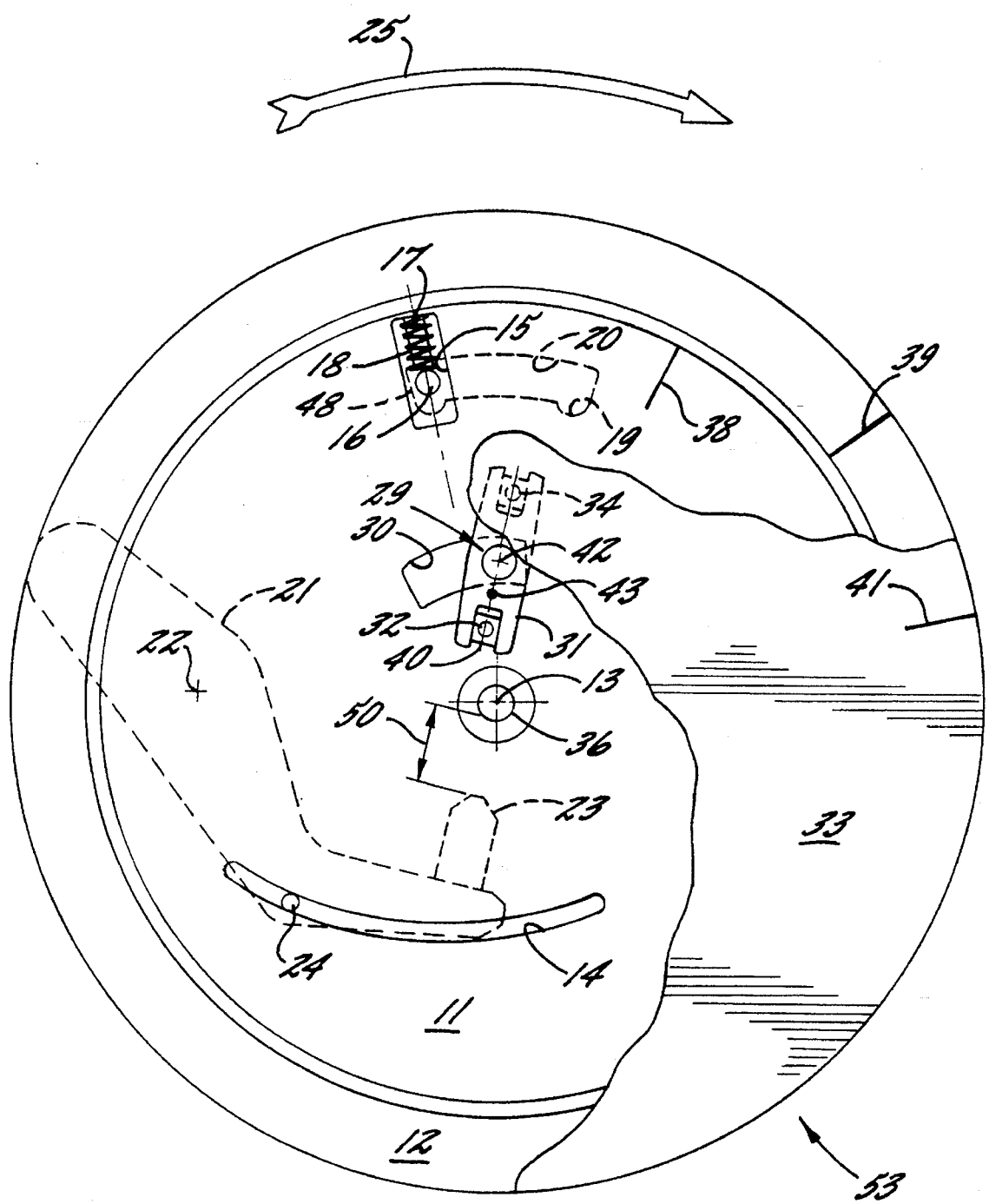
FIG. 5 A diagrammatic representation of the switching device in the raised position.

The function of the switching device is explained by means of FIGS. 3 to 5. A test object 36 with a circular cross-section is guided coaxially to the test head axis 13 through the head (FIG. 3). Upstream of the test head in the object running direction is provided a sensor (not shown), e.g. an optical, optoelectronic or mechanical sensor, which can detect cross-sectional irregularities of the test object, such as e.g. welding beads at the joint area of welded together wires and can provide control signals for the switching device.

With the rotor stationary, initially with the aid of a not shown frustum rack and pinion drive the diameter setting disk 12 and the spiral disk 11 are so rotated with respect to the rotor that the coupling pin 24 of the probe holding lever 21 runs along the spiral segment groove 14. This rotation, in particular of the spiral disk 11 with respect to the rotor, on which the probe holding lever 21 is mounted on its lever rotation axis 22, brings about a rotation of said lever about said axis 22, so that the probe 23 is displaced in roughly the radial direction towards or away from the object. The extent of this radial displacement as a function of the rotation angle of the spiral disk is dependent on the pitch of the spiral segment groove 14, which in FIG. 3, for illustration purposes, is steeper than that of the spiral segment grooves in FIG. 1. Setting takes place in such a way that between the active area of the probe 23 and the surface of the test object 36, a test spacing 37 is left.

During the diameter setting the centrifugal force coupling pin 16 is pressed by the coupling spring 17 positively into the recess 19 of the circular segment groove 20, so that the diameter setting disk 12 and the spiral disk 11 jointly rotate. In the testing position there is an alignment of the spiral disk marking 38 and the diameter setting disk marking 39 and the spiral disk journal 32 precedes the switching disk journal 34 in the rotation direction 25.

The spiral disk journal 32 and switching disk journal 34 engage by means of sliding holders 40 displaceably mounted in the change lever 31 on the latter and its mass centre of gravity 43 (diagrammatically indicated by the black circle representing an additional weight on the corresponding side of the change lever) does not coincide with its rotation axis 42 (cf. FIG. 4). The position of the change lever 31 also fixes the relative rotation of the switching disk 33 with respect to the spiral disk 11. This position is illustrated by the switching disk marking 41.

When the test head rotor starts to rotate about the test head axis 13 in the direction of the rotation direction arrow 25, the spiral disk 11, the diameter setting disk 12, the switching disk 33, as well as the probe holding lever 21 mounted on the rotor and whereof only one together with the test probe 23 held by it is shown, as well as the change lever 31, mounted in rotary manner on the reversing means journal 29 of the diameter setting disk 12, all rotate at the same speed and in the same direction. The active areas of the probe 23 rotate with the test spacing 37 from the surface of the object 36 and around the latter.

With increasing rotational speed the centrifugal forces acting on all the parts of the switching device increase. On exceeding a certain rotor speed, the centrifugal force acting on the centrifugal force coupling pin 16 is higher than the counterforce applied by the coupling spring 17 also influenced by the centrifugal forces, so that the centrifugal force coupling pin is forced along the recess 15 radially outwards against the stop pin 18. Therefore the diameter setting disk 12 and the spiral disk 11 are decoupled in the vicinity of the coupling pin.

However, even following decoupling the rotation position of the spiral disk 11 with respect to the diameter setting disk is still clearly defined and stabilized by centrifugal forces in the vicinity of the centrifugal force coupling pin. This is illustrated by FIG. 4, which diagrammatically shows a centrifugal force-stabilized switching state of the switching device. The change lever 31 is mounted in rotary manner on the reversing means journal about the reversing means rotation axis 42. The mass centre 43 of the change lever 31 is removed from the reversing means rotation axis 42 by the spacing 44. In practice this can e.g. be achieved by an asymmetrical shaping of the reversing or change member, e.g. in that the facing lever arms are given different thicknesses.

On rotating the reversing means about the test head axis 13 the centrifugal force directed in the direction of the arrow 45 brings about a torque on the change lever across the spacing 44. In the position of the change lever indicated by continuous lines and corresponding to that of FIG. 3, said torque is able to rotate the change lever counter to the rotation direction 25 of the rotor, which via the spiral disk journal 32 corresponds to a rotation of the not shown spiral disk in the direction of the rotation direction arrow 25. This rotation is limited by the striking of the centrifugal force coupling pin 16 against a side wall 46 of the recess 19, so that the coupling pin is pressed by the torque against the side wall 46. Provided via the switching disk journal 34 the rotation position of the switching disk 33 is fixed in the position shown in FIG. 3 and stabilized by the centrifugal force acting on the change lever 31.

On operation of an eddy current brake acting on the spiral disk 11, in the case of an adequate braking capacity, its rotation speed is slowed down compared with the test head rotor, which with respect to the rotating rotor corresponds to a relative movement of the spiral disk counter to the rotation direction 25 of the test head. As a result of the deceleration a force directed counter to the rotation direction 25 acts on the spiral disk journal 32 and via the journal spacing 47 brings about a torque on the change lever 31, which is directed counter to that brought about by the centrifugal forces. In the case of a specific braking capacity this torque exceeds that brought about by the centrifugal force and the change lever 31 in the direction of the rotation direction arrow 25 is overturned into the direction of the position shown in broken line form in FIG. 1. The change lever 31 overcomes an unstable position, in which the mass centre 43 and the reversing means rotation axis 42 are aligned with one another as from the test head axis 13.

On passing beyond this unstable position the torque brought about by the braking and that by the centrifugal force act in the same direction on the change lever, namely towards the broken line position. Therefore the braking action is only necessary until the unstable position of the switching device is exceeded. If the change lever is in the broken line position, then the centrifugal force coupling pin 16 is pressed against the side wall 48 of the circular segment groove 20.

The rotation of the change lever 31 towards the rotation direction 25 initiated via the braking of the spiral disk 11, by means of the switching disk journal 34 leads to a relative rotation of the switching disk 33 with respect to the spiral disk 11 in the direction of the rotation direction arrow 25 and a relative rotation of the spiral disk 11 with respect to the diameter setting disk 12 counter to the rotation direction 25. This rotation is limited by the centrifugal force coupling pin 16 striking against the side wall 48 of the circular segment groove 20, so that the spiral disk 11 is rotated with respect to the diameter setting disk 12, in which the circular segment groove 20 is provided, by the control angle 49 counter to the rotation direction 25. This position of the switching device illustrated in broken line form is shown in FIG. 5. Compared with the position of FIG. 3, in the case of an unchanged position of the diameter setting disk with respect to the test head (illustrated by the diameter setting disk marking 39), the spiral disk 11 with the spiral disk marking 38 has moved counter to the direction 25 and the switching disk 33 with the switching disk marking 41 in the rotation direction 25.

The spiral segment groove 14 has also moved counter to the rotation direction 25, so that the coupling pin 24 is now positioned on a radially further outwardly located position of the spiral segment groove 14. Correspondingly the probe holding lever 21 has rotated about the lever rotation axis 22 in the rotation direction 25, so that the probe 23 now has a spacing from the object surface corresponding to the raised position. This switching state is equivalent in energy to that of FIG. 3 and is only stabilized by centrifugal forces.

If the cross-sectional irregularity area has passed through the test head and the object again has its desired cross-section, then this change is also detected by the sensor and a return signal is transmitted to the switching device. For resetting the testing device into the testing position shown in FIG. 3, a brief braking of the switching disks 33 is now necessary. In the described way, this brings about a rotation of the change lever 31 counter to the rotation direction 25 over and beyond the stable position and back into the testing position shown in FIG. 3.

Numerous known means can be used for showing or displaying the particular switching state of the device. Thus, optical detectors could detect and display to the outside the position of the markings (similar to the markings 38, 39 and 41) on the control elements. The position of the change lever 31 and/or the centrifugal force coupling pin 16 and/or the probe holding lever 21 could be used for displaying the switching state by e.g. electrically, electronically or electro-magnetically operating sensing means.

Thus, the invention provides a mechanical flip-flop device, which can very rapidly switch over or reverse. The switching speed is dependent on the mass of the control elements to be moved on switching over, apart from the rotor rotation speed. If these masses are kept small, then on the one hand the bearings can be made smaller, so that the frictional forces to be overcome are reduced, and on the other hand the smaller forces are adequate for accelerating the control elements and therefore for the reversing thereof. However, as a condition when designing the control elements, it must be borne in mind that they are exposed to enormous centrifugal forces, so that there must be a corresponding stability against elastic and possibly even plastic deformation.

The operational reliability of the device is also helped by a compressed gas supply to or a compressed gas removal from the area of the probes rotating about the test object. This can be used on the one hand for keeping the test area clean, particularly with respect to metallic impurities which could interfere with the test signals, and on the other hand by supplying compressed gas the device can be cooled and despite the continuously produced frictional heat can always be kept at a constant operating temperature, which is advantageous with respect to the thermal expansion of the individual elements in the sense of constant testing conditions.

Figure 6:
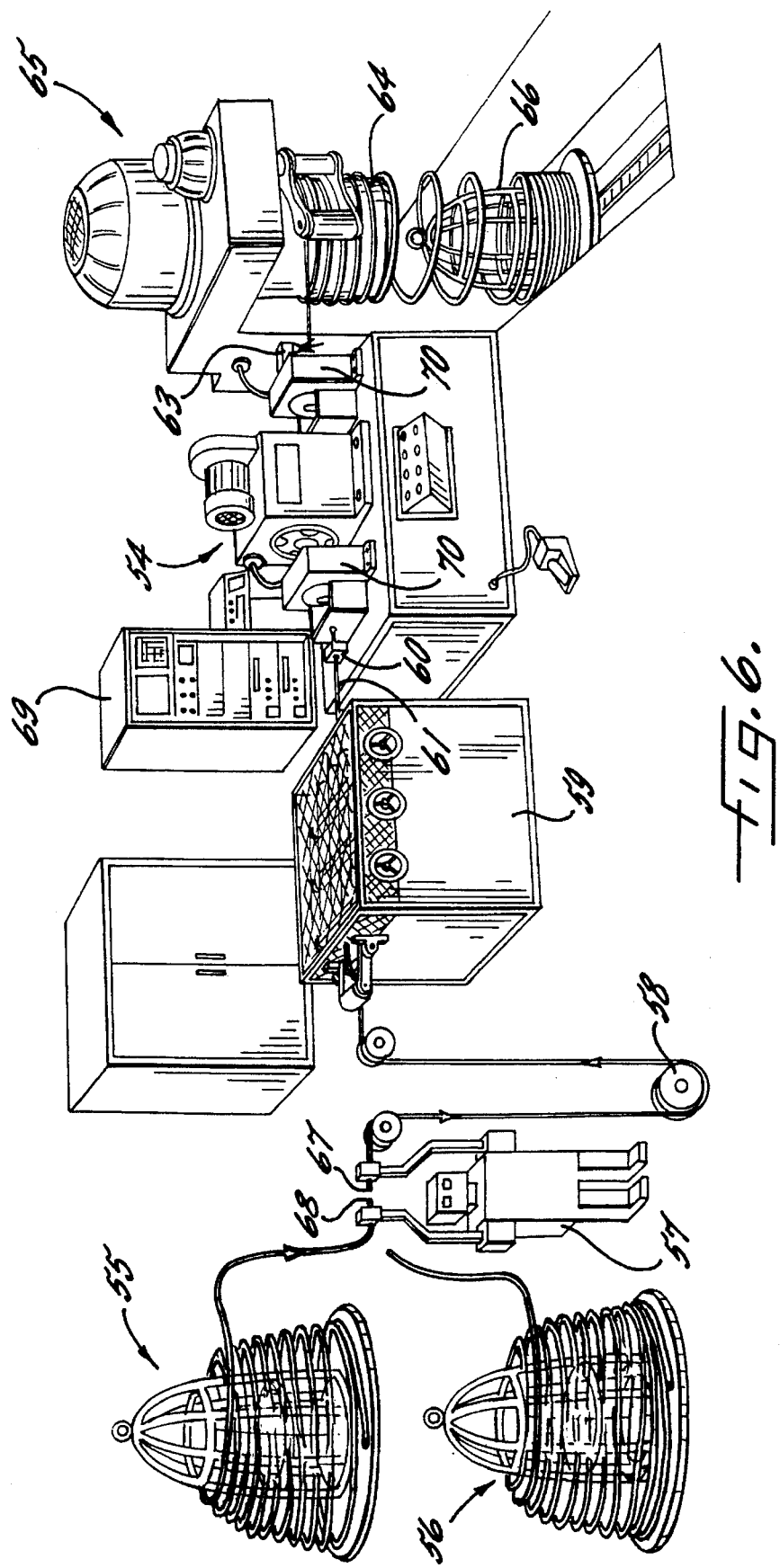
FIG. 6 A diagrammatic view of the testing device integrated into a continuously operating wire drawing plant.

In practice a continuously operating wire drawing plant with integrated testing device 54 can be constructed e.g. in the manner shown in FIG. 6. On the entrance side of the testing device are provided a first wire roll 55 and a second wire roll 56, the wire for the drawing process initially being unrolled from the roll 55, guided through the area of a welding robot 57 and a wire storage device 58 and into a wire drawing device 59. In the wire passage direction behind the wire drawing device 59 there is a sensor 60 associated with the testing device 54 and which in the case of cross-sectional irregularities of the wire 61 passing out of the wire drawing device 59, optionally via the control and evaluating unit 69, emits a switching signal to the testing device 54.

Upstream and downstream of the testing device 54 are fitted drawing or guidance nozzles 70. Behind the outlet-side drawing or guiding nozzle is provided a marking device 63, which marks with sprayed paint those drawn wire areas which have either been detected as faulty by the testing device, or which have not been tested, because they have passed through the test head at a time in which the switching device was in the raised position of the probe. In order to ensure the necessary quality such plants are operated on the basis of the principle "untested =faulty". The drawn, tested and optionally marked wire is then rolled onto the drum 64 of the drawing motor 65 and drops from there onto an outlet wire roll 66.

In the represented embodiment the wire end 67 of a wire which has just passed through the drawing process reaches the area of the welding robot 57 and is secured there. The wire start 68 of the wire wound onto the roll 55 is welded to the wire end 67. During the welding process wire from the wire storage means 58 passes into the drawing device, which can therefore operate at an unchanged speed during welding. Following the welding process the weld point provided with a welding bead and possibly a wire displacement passes through the wire storage device 58 to the wire drawing device 59 and there passes through the wire drawing nozzles. The welding point is relatively uncritical for the wire drawing process, but e.g. the welding bead could destroy in the case of contact the sensitive probes rotating at high speed and at only a limited distance around the wire. When the bead point reaches the sensor 60, the latter emits a switching signal to the testing device 54 and then the latter rapidly brings the probes into the raised position. In the case of typical wire passage speeds of approximately 3 m/s, the switching process must follow the detection of the cross-sectional irregularity by the sensor 60 in fractions of a second. As soon as the probes are moved away from the wire, the marking device 63 marks the untested wire point, which is then not used further.

After a cross-sectional irregularity has passed through the sensor 60, the latter again generates a desired or nominal signal and again switches the switching device, so that the probes again return to their testing position. This resetting takes place in the case of the present device with high reproduction precision, so that prior to raising and after resetting of the probes the control and evaluating unit 69 of the testing device essentially receives signals having the same intensity.

We claim:

1. An apparatus for testing elongated objects which possibly have cross-sectional irregularities, comprising:

a rotary test head which is adapted to rotate around a rotation axis, the rotary test head comprising a rotor having a central opening through which an object is adapted to pass while moving along the rotation axis, and at least one probe holding means movably mounted on the rotor, at least one probe mounted on the one probe holding means, the one probe holding means with the probe being mounted such that upon rotation of the rotor the probe is guided on a circular probe path around the object and that there is a radial spacing between the object and the probe, and switching means for modifying the radial spacing between the object and probe while the rotary test head is rotating, the switching means including an adjusting means movably mounted with respect to the rotor and engaging the at least one probe holding means so that when the adjusting means moves relative to the rotor the probe holding means moves relative to the rotor, and reversing means operatively coupled to the adjusting means and acting thereon to selectively move the adjusting means relative to the rotor, the reversing means being movable between two switching positions which are inherently stable in a way that the switching positions can each be maintained without energy supply from the outside and are stabilized during rotation by centrifugal forces, whereby movement of the reversing means between said two positions acts to correspondingly move said adjusting means and said probe holding means, to thereby modify the radial spacing between the object and probe.

2. The apparatus according to claim 1, wherein the one probe holding means together with at least one probe mounted thereon has a center of gravity and is mounted on the rotor to be rotatable around the center of gravity, whereby the radial spacing is adjustable by rotating the probe holding means.

3. The apparatus according to claim 1, wherein the adjusting means comprises a control disk (11) which is rotatably mounted and is coaxially arranged with the rotor and rotatable with respect to the rotor and engages the one probe holding means through coupling means.

4. The apparatus according to claim 3, wherein the coupling means comprises at least one spiral segment groove formed in said control disk and passing in a spiral segmental manner around the rotation axis, and a coupling member fixed on the one probe holding means remote from the rotation axis of the one probe holding means and engaging the groove.

5. The apparatus according to claim 3, wherein the reversing means includes at least one reversing member engaging said control disk, the reversing member having a center of gravity and being rotatably mounted outside the center of gravity and being limited in rotation.

6. The apparatus according to claim 1, wherein the reversing means is switchable by an energy pulse.

7. The apparatus according to claim 1, wherein the reversing means is switchable by an energy pulse using energy pulse transmitting means constructed as an eddy current brake and which acts in a contactless manner.

8. The apparatus according to claim 3, wherein said switching means further includes an adjusting drive disk (12) rotatably mounted coaxially to the rotor and rotatable with respect thereto, and means interconnecting the adjusting drive disk (12) and the control disk (11) so as to permit limited rotational movement therebetween.

9. The apparatus according to claim 8, wherein the means interconnecting the adjusting drive disk (12) and the control disk (11) comprises a centrifugal force decoupling means comprising a centrifugal force coupling pin movably guided in the control disk in a substantially radial direction and subject to a force acting radially inward applied through an elastic element provided on the control disk, and which upon rotation of the rotor is moved by centrifugal force out of the positive engagement in the control disk in a radially outward direction.

10. The apparatus according to claim 8, wherein the switching means further includes a switching disk (33) rotatably mounted coaxially with the rotor and rotatable with respect to the rotor and with respect to the control disk (11), the switching disk (33) and the control disk (11) being coupled by a reversing member (31) so as to provide a rotation direction reversing coupling between the switching disk (33) and the control disk (11).

11. The apparatus according to claim 10, wherein the reversing member (31) is rotatably mounted to the adjusting drive disk (12) and so as to engage the control disk (11) and the switching disk (33).

12. The apparatus according to claim 11, wherein the switching means further includes at least one eddy current brake acting in contactless manner on the switching disk (33) and on the control disk (11) and braking the rotational movement thereof during actuation.

13. The apparatus according to claim 1, wherein the probe is an eddy current probe.

14. The apparatus according to claim 1, wherein the probe has a longitudinal axis and has a zone of optimum action centrally on the longitudinal axis and wherein the probe is oriented with the zone of optimum action substantially radially to the object over a limited rotation range of the one probe holding means.

15. The apparatus according to claim 1, further comprising means for indicating the switching state of the switching means.

16. The apparatus according to claim 1, further comprising sensor means for detecting cross-sectional irregularities of the object at a location upstream of the rotary test head in the running direction of the object and for activating the switching means in response thereto and so as to switch between the two switching states.

* * * * *